United States Patent
Howison et al.

(10) Patent No.: US 8,209,054 B2
(45) Date of Patent: Jun. 26, 2012

(54) HAPTIC DEVICE GRIPPERS FOR SURGICAL TELEOPERATION

(76) Inventors: William Howison, Dallas, TX (US); Ryder Winck, Atlanta, GA (US)

(*) Notice: Subject to any disclaimer, the term of this patent is extended or adjusted under 35 U.S.C. 154(b) by 644 days.

(21) Appl. No.: 12/463,277

(22) Filed: May 8, 2009

(65) Prior Publication Data
US 2009/0287351 A1   Nov. 19, 2009

Related U.S. Application Data

(60) Provisional application No. 61/051,848, filed on May 9, 2008.

(51) Int. Cl.
*G06F 19/00* (2011.01)

(52) U.S. Cl. ........... 700/245; 318/560; 318/568.12; 318/568.16; 318/568.2; 318/568.21; 901/1; 901/2; 901/9; 901/19; 901/27; 901/30; 901/33; 901/34

(58) Field of Classification Search ............. 700/245; 318/560, 568.12, 568.16, 568.2, 568.21; 901/1, 2, 9, 19, 27, 30, 33, 34
See application file for complete search history.

(56) References Cited

U.S. PATENT DOCUMENTS

| | | | | |
|---|---|---|---|---|
| 2001/0000663 A1* | 5/2001 | Shahoian et al. | | 345/156 |
| 2001/0019324 A1* | 9/2001 | Rosenberg | | 345/156 |
| 2007/0296366 A1* | 12/2007 | Quaid et al. | | 318/568.16 |
| 2008/0010705 A1* | 1/2008 | Quaid et al. | | 901/8 |

OTHER PUBLICATIONS

Zemiti et al., Mechatronic Design of a New Robot for Force Control in Minimally Invasive Surgery, Apr. 2007, IEEE/ASME Transactions on Mechatronics, vol. 12, No. 2, pp. 143-153.*
Katsura et al., Medical mechatronics—An application to haptic forceps, 2005, Annual Reviews in Control, vol. 29, Issue 2, pp. 237-245.*
Mitsuishi, Mamoru, Force-Feedback Augmentation Modes in the Laparoscopic Minimally Invasive Telesurgical System, Aug. 2007, IEEE/ASME Transactions on Mechatronics, vol. 12, No. 4, pp. 447-454.*
12463277 EIC 3600 search results.*

* cited by examiner

*Primary Examiner* — Khoi Tran
*Assistant Examiner* — Jamie Figueroa
(74) *Attorney, Agent, or Firm* — Howison & Arnott, L.L.P.

(57) ABSTRACT

An embodiment of a haptic gripper system includes a slave gripper device, a master gripper device, and a gripper motor controller. The gripper motor controller includes a slave encoder loop, a master encoder loop, and a haptic loop. The haptic loop is configured to receive a slave motor encoder loop output signal and a master motor encoder loop output signal, determine a difference signal between the slave motor encoder loop output signal and the master motor encoder loop output signal representative of a difference between a first relative angular position of a slave gripper motor and a second relative angular position of a master gripper motor, and provide a slave motor control signal to a slave motor control signal input, and provide a master motor control signal to the master motor control signal input. The slave motor control signal and the master motor control signal drive at least one of the slave gripper motor and the master gripper motor to match their respective relative angular positions with respect to the other.

2 Claims, 10 Drawing Sheets

FIG. 11

HAPTIC DEVICE GRIPPERS FOR SURGICAL TELEOPERATION

CROSS-REFERENCE TO RELATED APPLICATIONS

This application is a non-provisional application of U.S. Provisional Application for Patent Ser. No. 61/051,848, filed May 9, 2008, and entitled HAPTIC DEVICE GRIPPERS FOR SURGICAL TELEOPERATION, the specification of which is incorporated herein by reference in its entirety.

BACKGROUND

Laparoscopic surgery provides a number of advantages over invasive surgery. The use of surgical robotics in laparoscopic procedures provides further advantages to both surgeons and patients. Laparoscopic surgery, also known as minimally invasive surgery, involves making small incisions (approximately 1-2 cm long) into the patient and then inserting a long, thin instrument with a variety of tools attached to the end. A camera is similarly inserted into the operation area to provide visual feedback during the operation. Although much trauma to the patient's body is avoided and blood-loss is reduced, there remain notable disadvantages to laparoscopy. Due to the position of the critical organs, possible avenues in the body cavity through which to gain access to the operation site are limited and can necessitate the surgeon operating his tools while in an awkward position. For example, the surgeon may be required to operate with tools that are inserted on opposite sides of the body, requiring each of his/her arms to be wrapped around the body of a patient. Furthermore, maintaining a proper view of the monitor displaying the video feed during the operation while manipulating the surgical tools is yet another challenge.

The da Vinci® robot by Intuitive Surgical is a commercially available surgical robot that allows a surgeon at a control station to remotely manipulate a set of robotic arms tipped with various tools. This control scheme, while still somewhat artificial, is more intuitive than direct manipulation of laparoscopic instruments. The control station provides 3-D stereoscopic visual feedback via a pair of cameras inserted at the operation site. The video display is positioned above the gripper controls so that the surgeon sees the grippers moving in the same plane as his hands. The surgeon sits down while operating, resulting in reduced stress as well as a more natural body position. The main limitation with the da Vinci system is that the master controls provide little to no force feedback. As a result, the surgeon may have difficulty obtaining a realistic feel of the forces that he or she is exerting with the robotic end effectors. Anecdotal evidence reveals that the da Vinci® robot is capable of easily rupturing tissue or breaking sutures and, as a result, many surgeons do not feel comfortable using the device due to the lack of feedback communicating the amount of force they are applying.

SUMMARY

An embodiment of a haptic gripper system includes a slave gripper device, a master gripper device, and a gripper motor controller. The slave gripper device includes a slave robot body portion, a slave arm having a first slave arm end coupled to the slave robot body portion, and a slave elbow joint coupled to a second slave arm end of the slave arm. The slave elbow joint has a slave elbow joint hinge pin having a substantially circular cross-section and a first horizontal axis of rotation. The slave elbow joint hinge pin further has a plurality of slave elbow cable channels. Each slave elbow cable channel has an upper surface with a substantially parabolic cross section and a vertex positioned at a first predetermined distance below the first horizontal axis of rotation. The slave gripper device further includes a slave effector having first slave effector end coupled to the slave elbow joint, a slave gripper assembly coupled to a second slave effector end of the slave effector, and a slave gripper motor mounted to the slave arm. The slave gripper motor has a slave motor control signal input, and a first encoder configured to output a first slave motor encoder output signal and second slave motor encoder output signal. The slave gripper device further includes a slave drive cable coupled between the slave gripper motor and the slave gripper assembly through at least a first slave elbow cable channel of the plurality of slave elbow cable channels and in contact with the upper surface of the at least first slave elbow cable channel. The first predetermined distance is determined such that the slave drive cable passes substantially through the first horizontal axis of rotation of the slave elbow joint hinge pin.

The master gripper device includes a master robot body portion, a master arm having a first master arm end coupled to the master robot body portion, and a master elbow joint coupled to a second master arm end of the master arm. The master elbow joint has a master elbow joint hinge pin having a substantially circular cross-section and a second horizontal axis of rotation. The master elbow joint hinge pin further has a plurality of master elbow cable channels, wherein each master elbow cable channel has an upper surface with a substantially parabolic cross section and a vertex positioned at a second predetermined distance below the second horizontal axis of rotation. The master gripper device further includes a master effector having first master effector end coupled to the master elbow joint, a master gripper assembly coupled to a second master effector end of the master effector, and a master gripper motor mounted to the master upper link arm. The master gripper motor has a master motor control signal input, and a second encoder configured to output a first master motor encoder output signal and second master motor encoder output signal. The master gripper device further includes a master drive cable coupled between the master gripper motor and the master gripper assembly and routed through at least a first master elbow cable channel of the plurality of master elbow cable channels and in contact with the upper surface of the at least first master elbow cable channel. The second predetermined distance is determined such that the master drive cable passes substantially through the second horizontal axis of rotation of the master elbow joint hinge pin.

The gripper motor controller includes a slave encoder loop, a master encoder loop, and a haptic loop. The slave encoder loop having a first slave motor encoder input configured to receive the first slave motor encoder output signal, and a second slave motor encoder input configured to receive the second slave motor encoder signal. The slave encoder loop is further configured to determine a first relative angular position of the slave motor based upon the first slave motor encoder output signal and the second slave motor encoder output signal and output a slave motor encoder loop output signal indicative of the first relative angular position. The master encoder loop has a first master motor encoder input configured to receive the first master motor encoder output signal, and a second master motor encoder input configured to receive the second master motor encoder signal. The master encoder loop is further configured to determine a second relative angular position of the first master motor based upon the first master motor encoder output signal and the second master motor encoder output signal and output a master motor encoder loop output signal indicative of the second relative angular position.

The haptic loop is configured to receive the slave motor encoder loop output signal and the master motor encoder loop output signal, determine a difference signal between the slave motor encoder loop output signal and the master motor encoder loop output signal representative of a difference between the first relative angular position and the second relative angular position, amplify the difference value by a first gain factor to produce a slave motor control signal, amplify the difference value by a second gain factor to produce a master motor control signal, provide the slave motor control signal to the slave motor control signal input, and provide the master motor control signal to the master motor control signal input. The slave motor control signal and the master motor control signal drive at least one of the slave gripper motor and the master gripper motor to match their respective relative angular positions with respect to the other.

BRIEF DESCRIPTION OF THE DRAWINGS

For a more complete understanding, reference is now made to the following description taken in conjunction with the accompanying Drawings in which.

DETAILED DESCRIPTION

Referring now to the drawings, wherein like reference numbers are used herein to designate like elements throughout, the various views and embodiments of haptic device grippers for surgical teleoperation are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Various embodiments provide for a master and slave robotic system that provides haptic feedback, meaning a master gripper receives force information from a slave gripper and applies that force to a user or operator. Various embodiments provide for a teleoperation setup that allows for bilateral position-matching between the grippers of master and slave robots. That is the gripper of the master robot receives feedback from the gripper of the slave robot such that the user will feel resistance when force is applied to the slave robot. In various embodiments, the force feedback is applied to both the opening and closing of the grippers.

Figure 1:
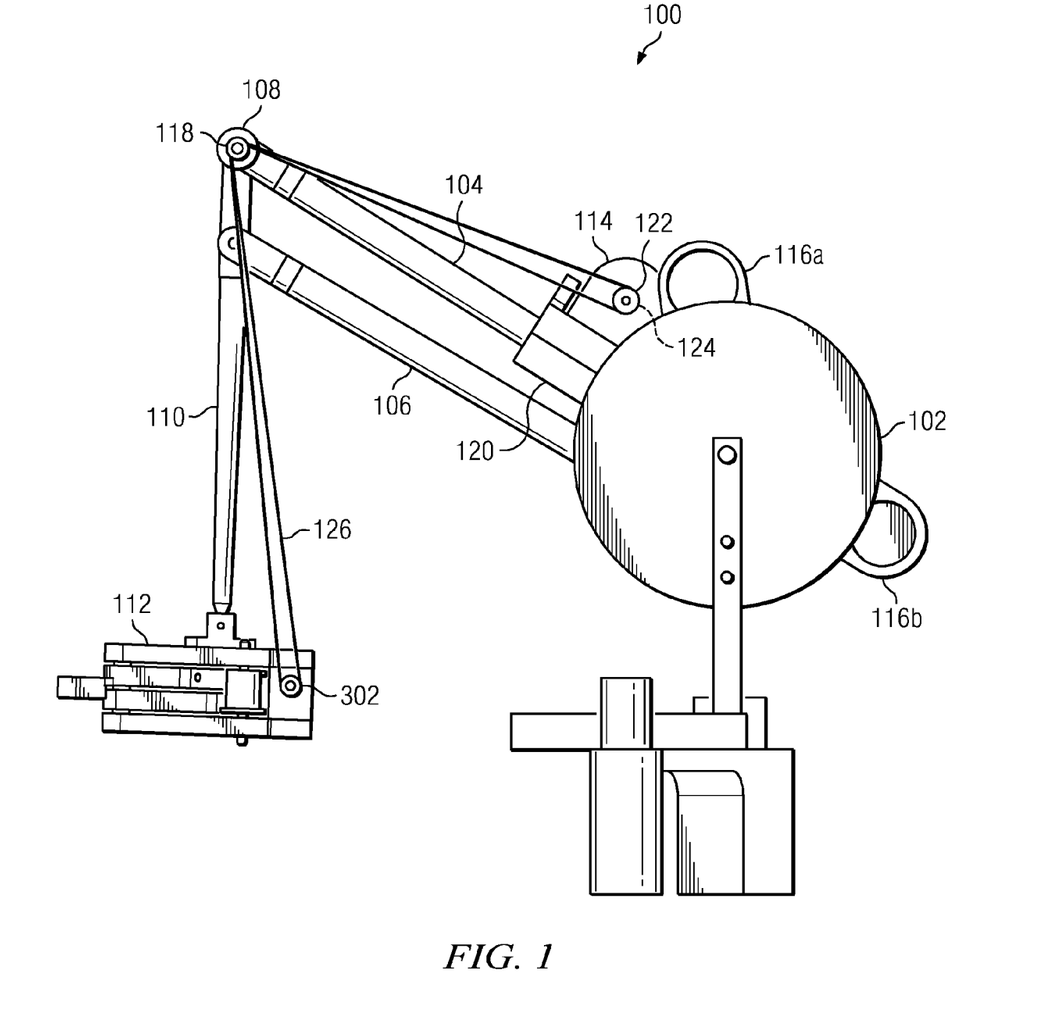
FIG. 1 illustrates an embodiment of a slave gripper device.

Referring now to FIG. 1, an embodiment of a slave gripper device 100 is illustrated. The slave gripper device 100 includes a slave robot body portion 102, a slave upper link arm 104, a slave lower link arm 106, a slave elbow joint 108, a slave effector 110, a slave gripper assembly 112, a slave gripper motor 114, and first and second slave counterweights 116a and 116b. In various embodiments, the slave robot body portion 102, the slave upper link arm 104, the slave lower link arm 106, and the slave effector 110 may be comprised of an existing robot that provides for three-degrees of freedom in the slave effector 110. In at least one embodiment, the robot may be a commercially available robot, such as a surgical robot. The slave upper link arm 104 has a first slave upper link end coupled to the slave robot body portion 102, and a second slave upper link end coupled to the slave elbow joint 108. The slave lower link arm 106 has a first slave lower link end coupled to the slave robot body portion 102 and a second slave lower link end jointedly coupled to the slave effector 110. The slave effector 110 has a first slave effector end coupled to the slave elbow joint 108, and a second slave effector end coupled to the slave gripper assembly 112. The slave elbow joint 108 further includes a slave elbow joint hinge pin 118. The first and second slave counterweights 116a and 116b are mounted on the slave robot body portion 102 to balance the weight of the slave gripper assembly 112 and slave gripper motor 114.

Figure 2A:
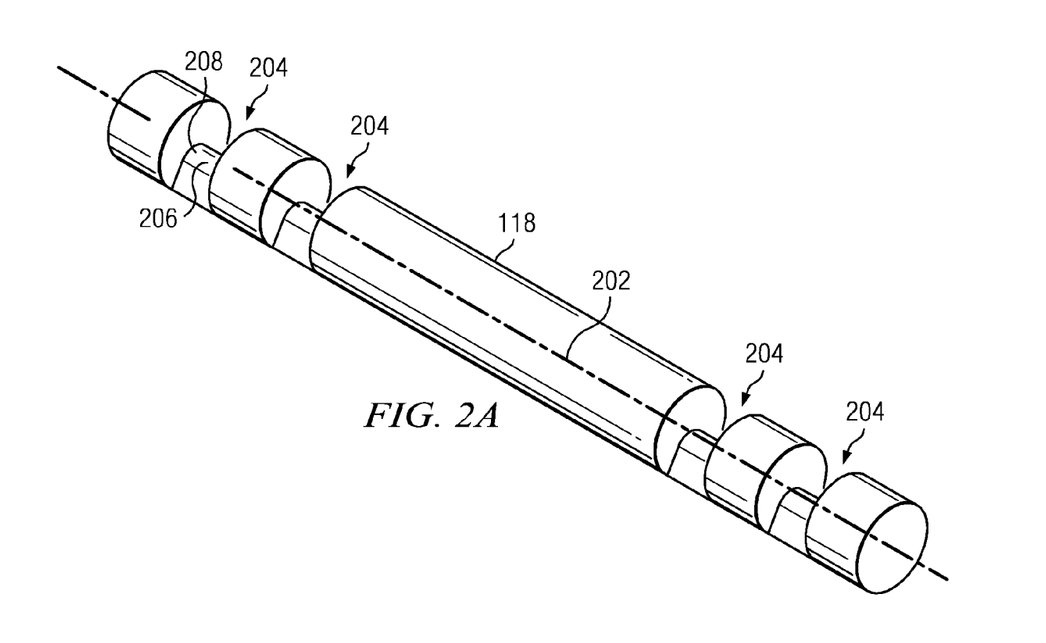
FIGS. 2A & 2B illustrate an embodiment of a slave elbow joint hinge pin of a slave elbow joint of FIG. 1.
Figure 2B:
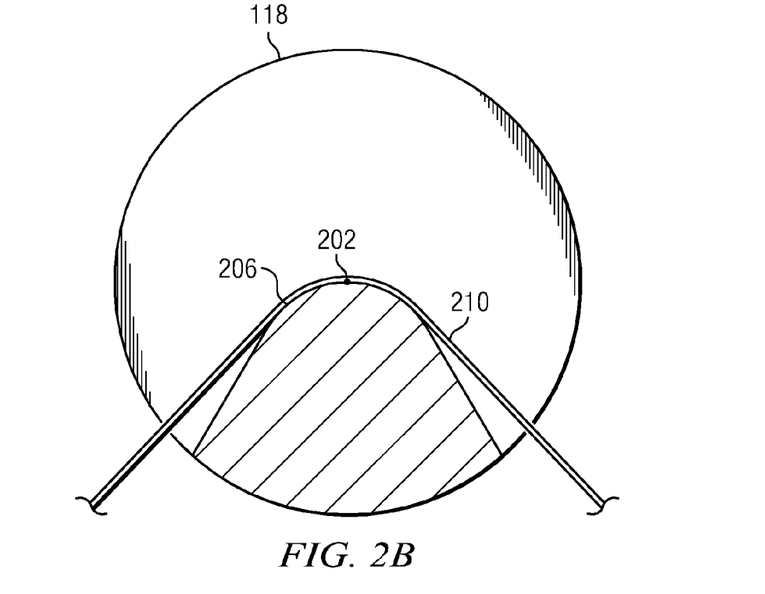

Referring now to FIGS. 2A & 2B, an embodiment of the slave elbow joint hinge pin 118 of the slave elbow joint 108 of FIG. 1 is illustrated. The slave elbow joint hinge pin 118 has a substantially circular cross-section and a first horizontal axis of rotation 202. The slave elbow joint hinge pin 118 has a plurality of slave elbow cable channels 204 formed therein. Each slave elbow cable channel 204 has an upper surface 206 having a substantially parabolic cross section and a vertex 208 positioned at a first predetermined distance below the horizontal axis of rotation 202. In the embodiment illustrated in FIG. 2A, the slave elbow joint hinge pin 118 includes four slave elbow cable channels 204. In a particular embodiment, the first predetermined distance is determined such that a drive cable 210 fed through the channel 204 and in contact with the upper surface 206 passes substantially through the first horizontal axis of rotation 202 of the slave elbow joint hinge pin 118. By providing for the drive cable 210 to pass through the first horizontal axis of rotation 202 of the slave elbow joint hinge pin 118, an arm angle between the slave upper link arm 104 and the slave effector 110 may be changed without substantially changing the tension in the drive cable 210.

Figure 3A:
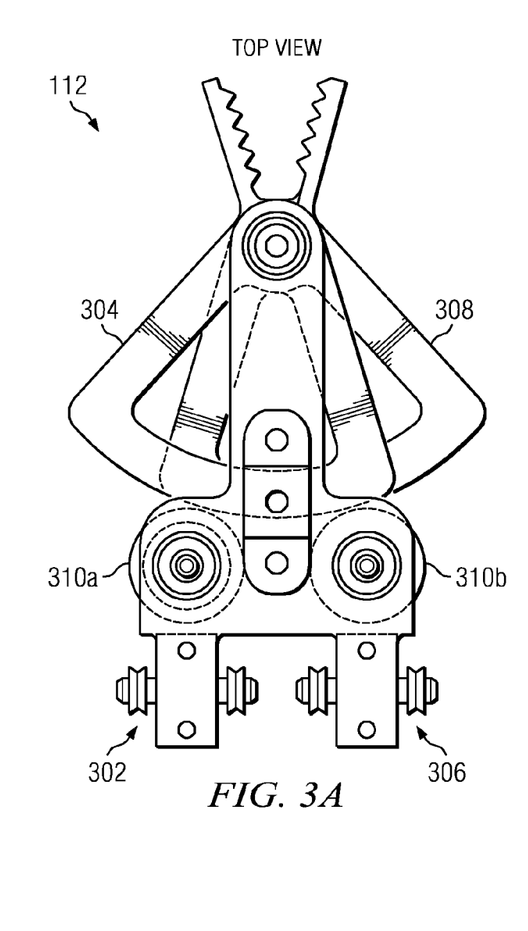
FIGS. 3A-3C illustrate an embodiment of a slave gripper assembly of FIG. 1.
Figure 3B:
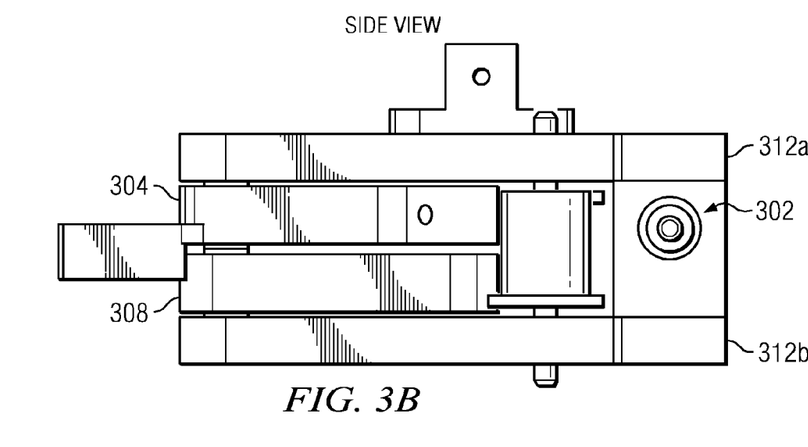
Figure 3C:
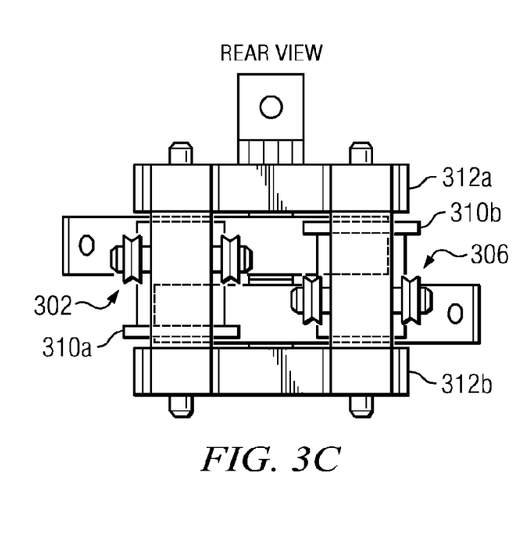

Referring now to FIGS. 3A-3C, an embodiment of the slave gripper assembly 112 of FIG. 1 is illustrated. FIG. 3A illustrates a top view, FIG. 3B illustrates a side view, and FIG. 3C illustrates a rear view of the slave gripper assembly 112. The slave gripper assembly 112 includes a first slave gripper spool 302 coupled to a first slave gripper arm 304 and a second slave gripper spool 306 coupled to a second slave gripper arm 308. The slave gripper assembly 112 consists of two slave cable drive capstans 310a and 310b mounted concentrically on a shaft and sandwiched by a slave gripper frame 312a and 312b.

Referring again to FIG. 1, the slave gripper motor 114 is mounted to the slave upper link arm 114 via a motor mount 120. The slave gripper motor 114 has a first slave motor pulley 122 on a first side and a second slave motor pulley 124 on a second side. A first slave drive cable 126 is coupled between the first slave motor pulley 122 and the first slave gripper spool 302 and is routed through a first slave elbow cable channel 204 and in contact with the upper surface 206 of the first slave elbow cable channel 204 in a forward direction, and routed through a second slave elbow channel 204 in a return direction. A second slave drive cable 128 is coupled between the second slave motor pulley 124 and the second slave gripper spool 306 and is routed through a third slave elbow cable channel 204 in a forward direction, and a fourth slave elbow cable channel 204 in a return direction. In a particular embodiment, each slave drive cable is wrapped around a slave motor pulley 122, 124 of the slave gripper motor 114, and around a slave gripper spool 302, 306 of the slave gripper assembly 112. The slave drive cable 126, 128 is further threaded through the two pulley joints and directed to a capstan portion of each slave gripper arm 304, 308. The capstans of each slave gripper arm 304, 308 are driven to rotate in opposite directions due to the slave drive cables being 126, 128 being mounted oppositely on each capstan wherein actuating the drive cables rotates each of the first slave gripper arm 304 and second slave gripper arm 308 in opposite directions so that the grippers can open and shut.

Figure 4:
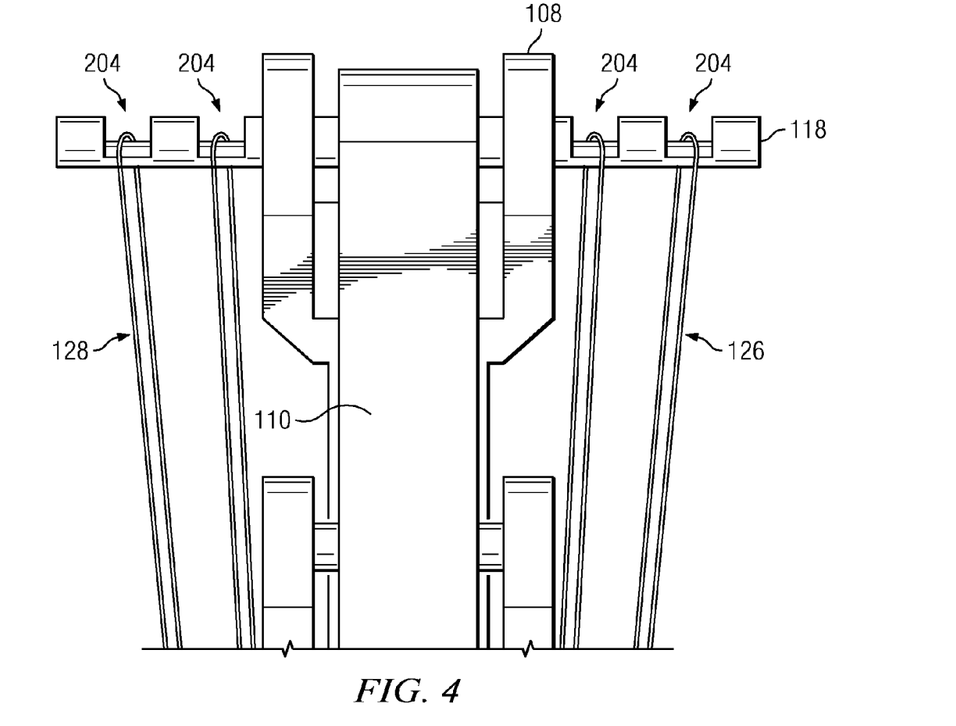
FIG. 4 illustrates a side view of the elbow joint hinge pin of FIG. 1 positioned within the slave elbow joint 108.

Referring now to FIG. 4, a side view of the elbow joint hinge pin 118 of FIG. 1 positioned within the slave elbow joint 108 is illustrated. FIG. 4 illustrates a particular embodiment of the routing of the first slave drive cable 126 and the second slave drive cable 128 through the slave elbow channels 204 of the elbow joint hinge pin 118. In the particular illustrated embodiment, the first slave drive cable 126 is routed through a first and second slave elbow channel 204, and the second drive cable 128 is routed through a third and fourth slave elbow channel 204 of the elbow joint hinge pin 118.

Figure 5A:
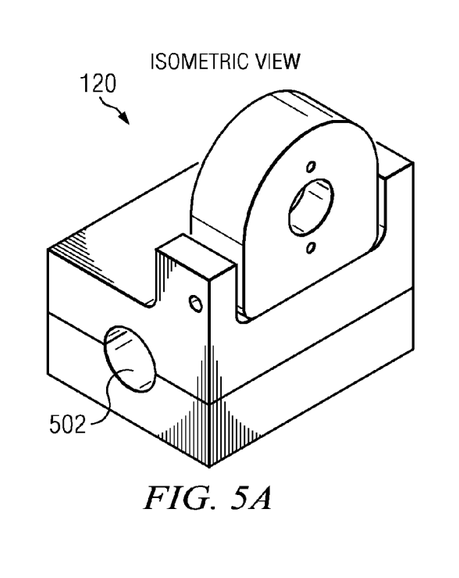
FIGS. 5A & 5B illustrate an embodiment of a motor mount of FIG. 1.
Figure 5B:
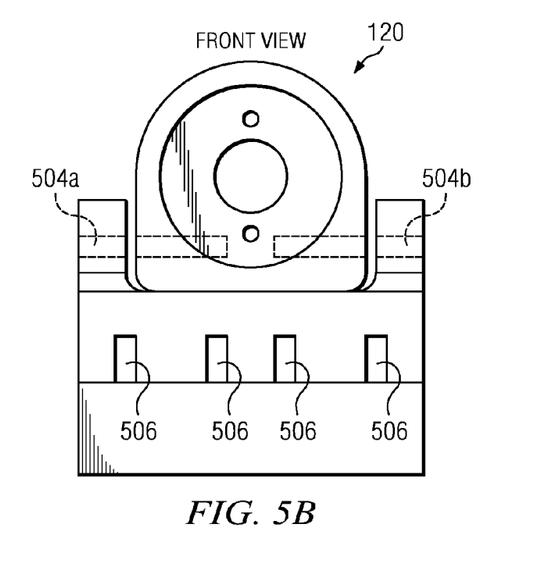

Referring now to FIGS. 5A & 5B, an embodiment of the motor mount 120 of FIG. 1 is illustrated. FIGS. 5A & 5B provide an isometric view and a front view of the motor mount 120, respectively. The motor mount 120 provides for an arm hole 502 to mount around the slave upper link arm 104. The motor mount 120 further includes tension screw holes 504a and 504b for accepting screws to attach the slave gripper motor 114 to the motor mount 120. After winding the slave drive cables 126, 128 around the slave motor pulleys 122, 14, the tension may be increased by loosening one screw and tightening the other until the desired tension is obtained. An inverse procedure may be used to allow the tension in the slave drive cables 126, 128 to be decreased. The motor mount 120 further includes a plurality of clamp screw holes 506 for accepting screws to clamp the motor mount 120 to the slave upper link arm 104.

Figure 6:
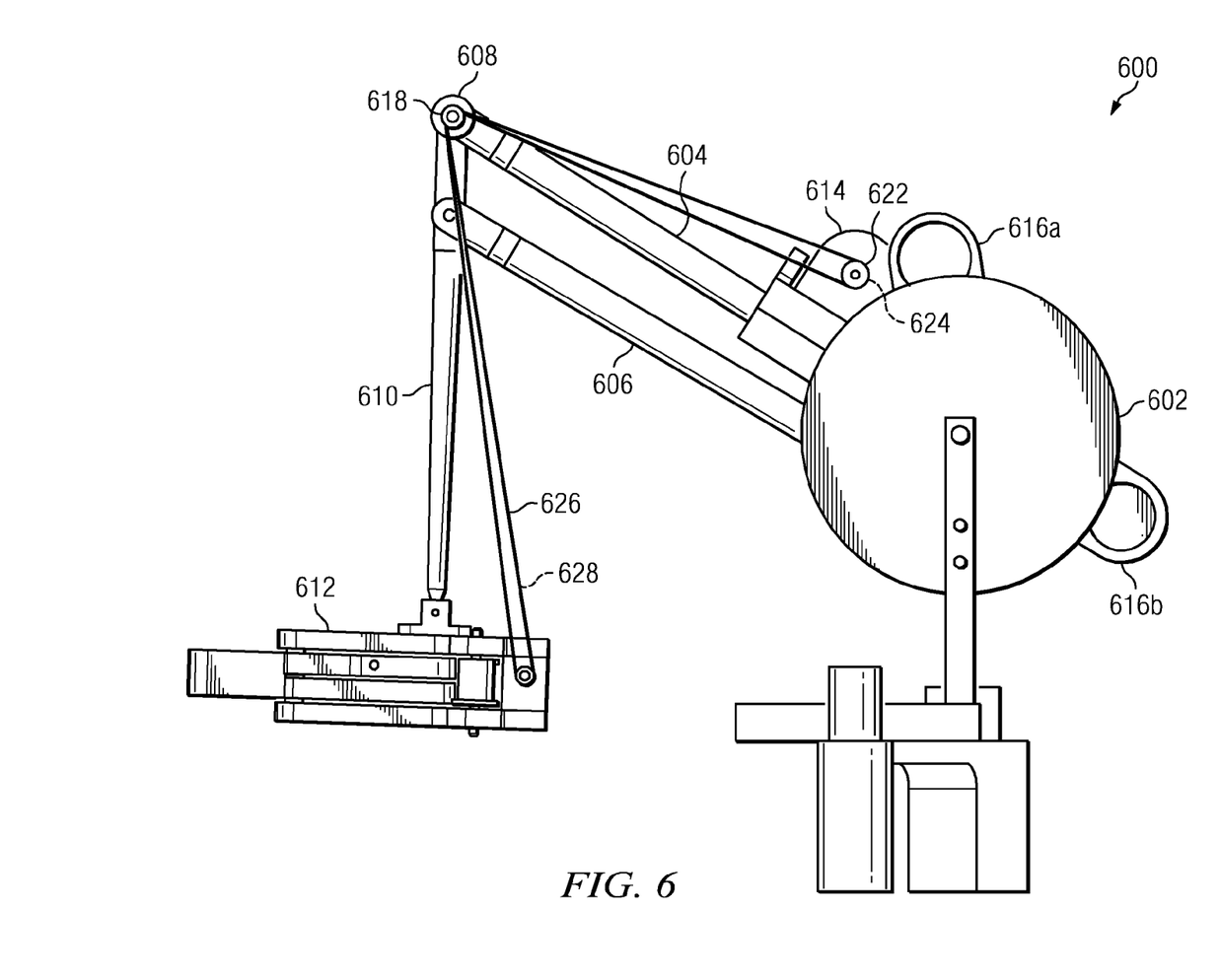
FIG. 6 illustrates an embodiment of a master gripper device.

Referring now to FIG. 6, an embodiment of a master gripper device 600 is illustrated. The master gripper device 600 is configured in a similar manner as the slave gripper device 100 except for that the master gripper assembly 612 has larger gripper arms than those of the slave gripper assembly, allowing a user to actuate a first master gripper arm 704 and a second master gripper arm 708. (Shown in FIGS. 7A-7C.) In a particular embodiment, each of the first master gripper arm 704 and the second master gripper arm 708 have a slot allowing a piece of Velcro® to be inserted and wrapped around a user's finger. The master gripper device 600 includes a master robot body portion 602, a master upper link arm 604, a master lower link arm 606, a master elbow joint 608 having a master elbow hinge pin 618, a master effector 610, a master gripper assembly 612, a master gripper motor 614, and first and second master counterweights 616a and 616b. In various embodiments, the slave robot body portion 602, the slave upper link arm 604, the slave lower link arm 606, and the slave effector 610 may be comprised of an existing robot that provides for three-degrees of freedom in the slave effector. In at least one embodiment, the master elbow hinge pin 618 is substantially the same as the slave elbow joint hinge pin 118 of FIGS. 2A & 2B.

Figure 7A:
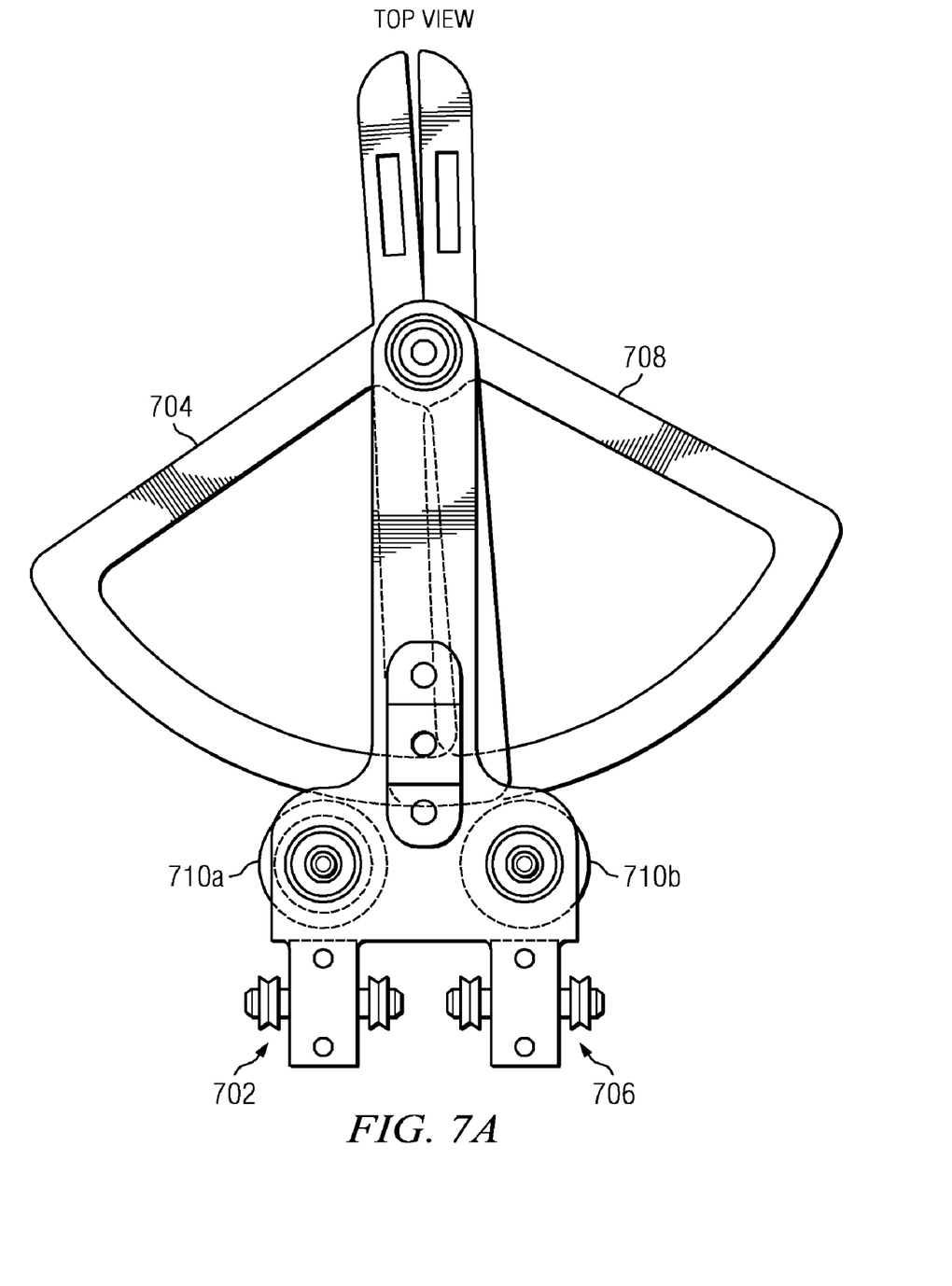
FIGS. 7A-7C illustrate an embodiment of a master gripper assembly of FIG. 6.
Figure 7B:
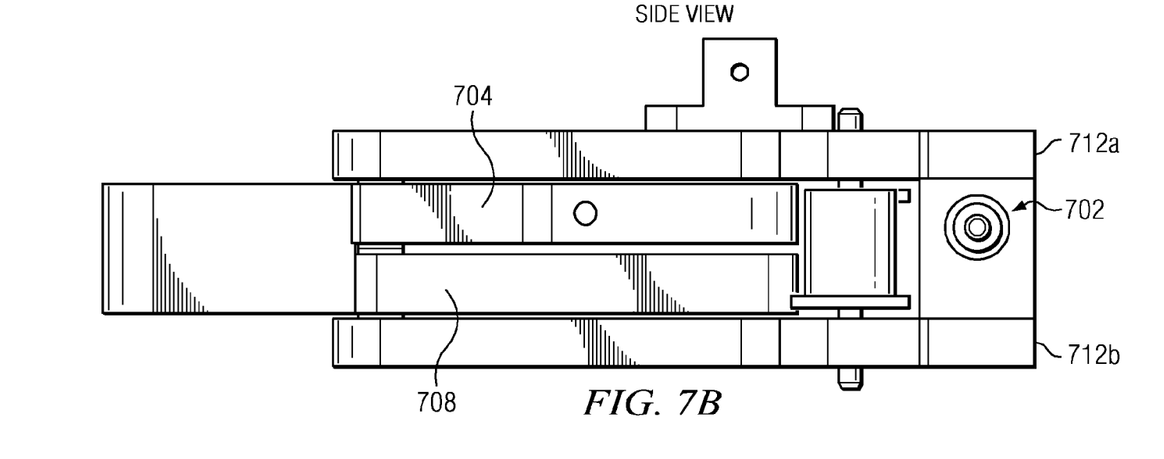
Figure 7C:
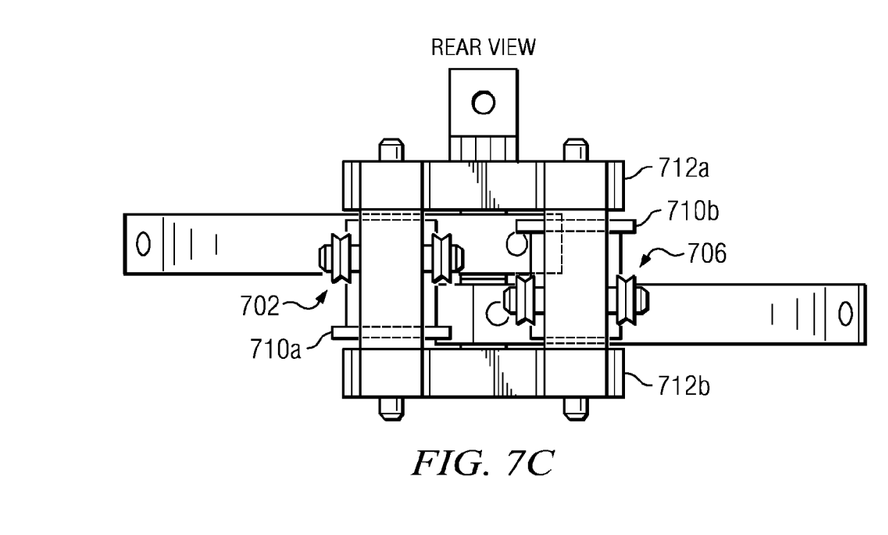

Referring now to FIGS. 7A-7C, an embodiment of the master gripper assembly 612 of FIG. 6 is illustrated. FIG. 7A illustrates a top view, FIG. 7B illustrates a side view, and FIG. 7C illustrates a rear view of the master gripper assembly 612. The master gripper assembly 612 includes a first master gripper spool 702 coupled to a first master gripper arm 704 and a second master gripper spool 706 coupled to a second master gripper arm 708. The master gripper assembly 612 consists of two slave cable drive capstans 710a and 710b mounted concentrically on a shaft and sandwiched by a master gripper frame 712a and 712b.

Referring again to FIG. 6, the master gripper motor 614 is mounted to the master upper link arm 604 via the motor mount 620. The master gripper motor 614 has a first master motor pulley 622 on a first side and a second master motor pulley 624 on a second side. A first master drive cable 626 is coupled between the first master motor pulley 622 and the first master gripper spool 702 and is routed through the master elbow joint hinge pin 618 in substantially the same manner as described with respect to the elbow joint hinge pin 618. A second master drive cable 628 is coupled between the second master motor pulley 624 and the second master gripper spool 706 and is routed through the master elbow joint hinge pin 618 in substantially the same manner as described with respect to the elbow joint hinge pin 618.

Figure 8:
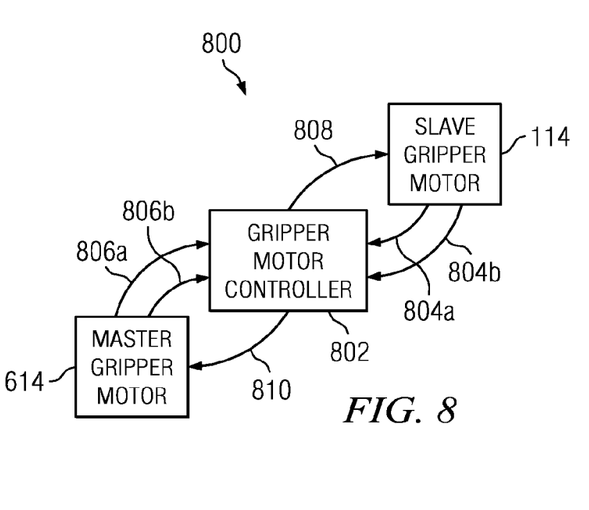
FIG. 8 illustrates an embodiment of a gripper motor control system.

Referring now to FIG. 8, an embodiment of a gripper motor control system 800 is illustrated. In various embodiments, the slave gripper device 100 and master gripper device 600 are connected in a master/slave configuration so that the slave gripper device 100 and master gripper device 600 mirror each other's movement of the slave effector 110 and master effector 610 in three dimensions. The gripper motor control system 800 includes a gripper motor controller 802, the slave gripper motor 114, and the master gripper motor 614. The gripper motor controller 802 is configured to receive information regarding the angular position of each of the slave gripper motor 114 and the master gripper motor 614, and performs position-matching control by commanding at least one of the gripper motor 114 and the master gripper motor 614 to change its position to match that of the other. In various embodiments, this provides an effect much like a virtual spring connecting the slave gripper motor 114 and the master gripper motor 614. When the controlling motor moves, the following motor tries to move with it, but at a slight delay and perhaps without reaching exactly the same relative point. The gripper motor controller 802 provides a bilateral system that performs this matching in both directions, so both motors are constantly trying to match the position of the other motor. This allows for an approximation of force feedback because the user or operator will control the movement of the slave by manipulating the master, but the operator will feel the slave's environmental interactions through the master in the same way. This allows the master gripper device 600 to receive feedback from the slave gripper device 100 such that the user will feel resistance when a force is applied to the slave robot's grippers. The force feedback is applied to both the opening and closing of the grippers.

Figure 9A:
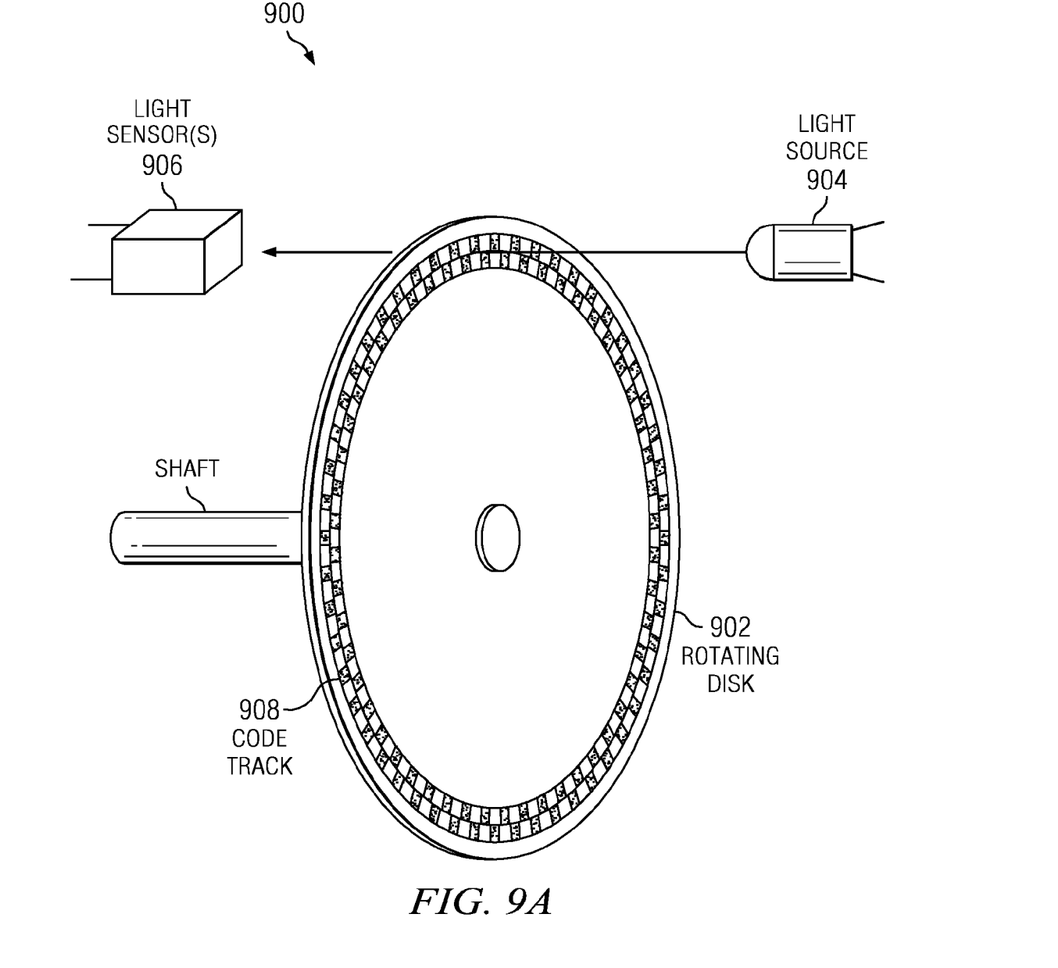
FIG. 9A illustrates an embodiment of a quadrature encoder.
Figure 9B:
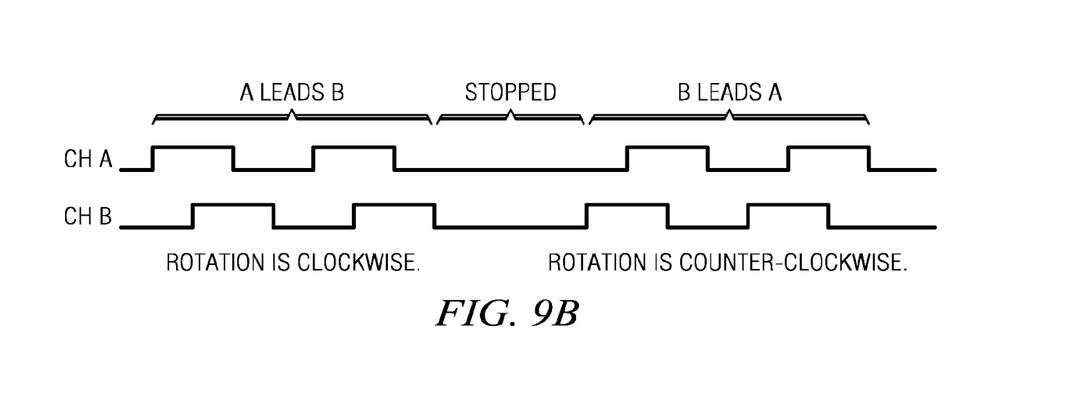
FIG. 9B illustrates a timing diagram of a quadrature encoder signal of the quadrature encoder of FIG. 9A.

Each of the slave gripper motor 114 and the master gripper motor 614 include a quadrature encoder configured to provide information regarding the angular position of the motor to be used for position matching. FIG. 9A illustrates an embodiment of a quadrature encoder 900. The quadrature encoder 900 includes a disk 902 that connects to the drive shaft of the gripper motor, a light source 904, and a light sensor 906. The disk 902 has two concentric circles of slits 908 forming a code track on which the light source 904 shines. As the shaft and disk 902 rotate, the light from the light source 904 is either let through a slit or blocked in-between slits. This light is read by the light sensor 906 and outputted as a digital signal (1 when light passes through the slit, 0 when it is blocked). The two rows of slits each provide a separate signal and the signals resulting from the rotation of the drive shaft are offset by 90 degrees in phase. A timing diagram of a quadrature encoder signal of the quadrature encoder 900 of FIG. 9A is illustrated in FIG. 9B. The signal timing is such that, while in continuous rotation, each cycle of the signal is one half the period of a pulse. Conversely, each pulse lasts 2 signal cycles. This is the key to measuring the position of the motor. The two signals are used by comparing the current cycle of one channel to the last cycle of the other channel. As may be seen in FIG. 9B, if the current cycle of channel A is the opposite value of the last cycle of channel B, the shaft is rotating clockwise. If the current cycle of A and the last cycle of B are the same, the shaft is rotating counter-clockwise. If the current cycles of both A and B are the same, the shaft is at rest. This allows provides for a reliable determination the position of the motor shafts and to this information is used for the position matching control system.

Referring again to FIG. 8, the gripper motor controller 802 includes a slave encoder loop, a master encoder loop, and a haptic loop. The slave encoder loop includes a first slave motor encoder input configured to receive the first slave motor encoder output signal 804b, and a second slave motor encoder input configured to receive the second slave motor encoder output signal 804b. The phase of the first slave motor encoder output signal 804a is offset by substantially 90 degrees from a phase of the second slave motor encoder output signal 804b. The slave encoder loop is further configured to determine a first relative angular position of the first slave motor based upon the first slave motor encoder output signal and the second slave motor encoder output signal, and output a slave motor encoder loop output signal indicative of the first relative angular position.

Figure 10:
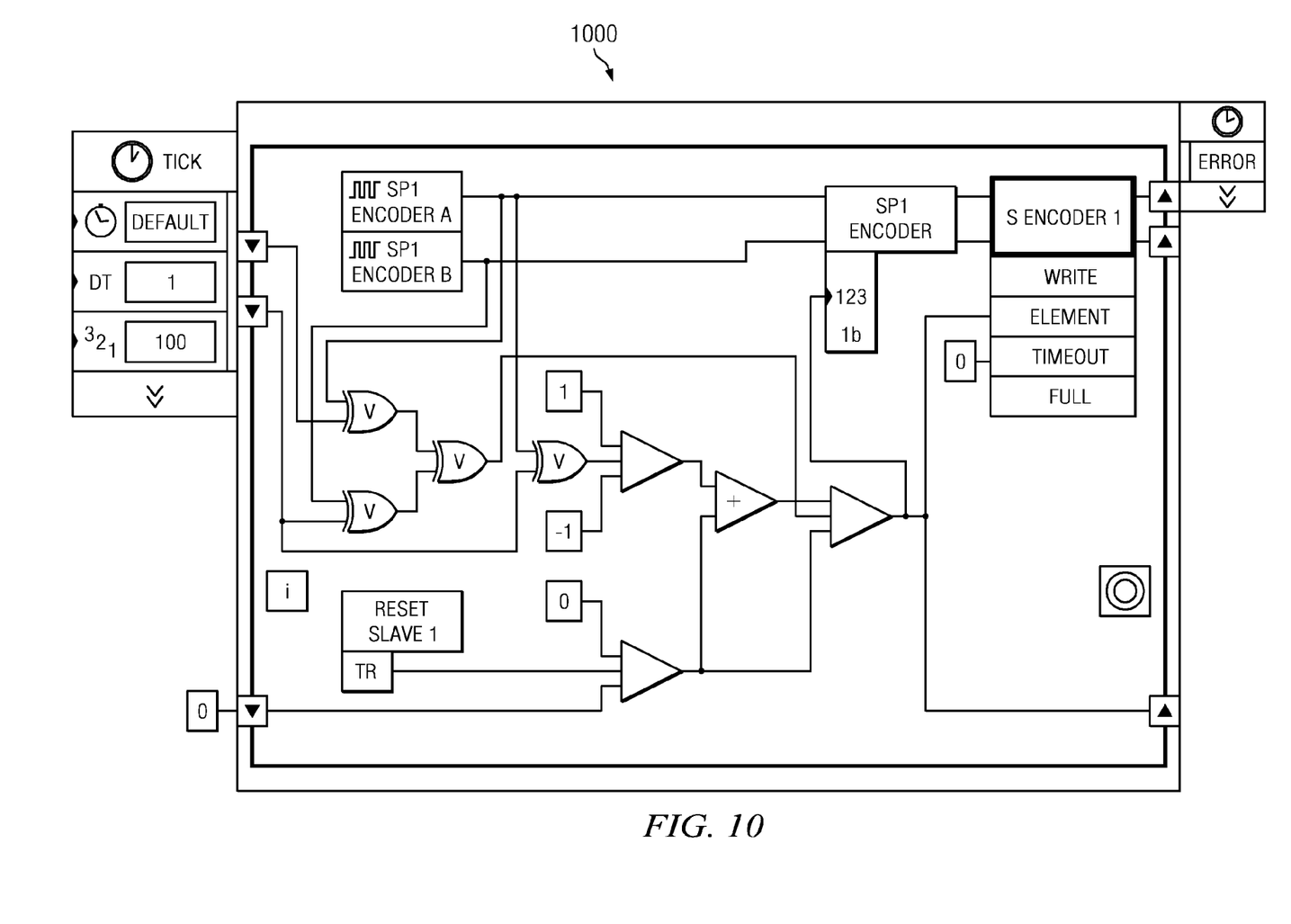
FIG. 10 illustrates an embodiment of a slave encoder loop.

An embodiment of a slave encoder loop 1000 is illustrated in FIG. 10. The slave encoder loop 1000 keeps a running counter that is 32 bits in depth to measure the encoder's position relative to its starting position. On each cycle of the loop this counter is incremented if the comparison code finds the shaft is rotating clockwise, and decremented if it is rotating counter-clockwise. If the shaft is stopped, the current value is left alone. A reset button is provided to allow the user or operator to set the slave gripper motor's current position as the new starting point. This feature allows both of the master gripper device 600 and slave gripper device 100 to be started at the same relative position (i.e. each of the arms of pointing the same way) or to reset the initial position of either the master gripper device 600 and slave gripper device 100 in case something causes them to get out of sync, such as mechanical slippage that would let the motor shaft reach the same angular position without carrying its load to the same position as that of its companion motor. The slave encoder counter is passed on by means of a FIFO register to the haptic loop.

The master encoder loop has a first master motor encoder input configured to receive the first master motor encoder output signal 806a, and a second master motor encoder input configured to receive the second master motor encoder signal 806b. The master encoder loop is further configured to determine a second relative angular position of the first master motor based upon the first master motor encoder output signal and the second master motor encoder output signal, and output a master motor encoder loop output signal indicative of the second relative angular position. In at least one embodiment, the master encoder loop is configured in the same way as the slave encoder loop illustrated in FIG. 10. The master encoder counter is passed on by means of a FIFO register to the haptic loop.

The haptic loop is configured to receive the slave motor encoder loop output signal and the master motor encoder loop output signal, and determine a difference signal between the slave motor encoder loop output signal and the master motor encoder loop output signal representative of a difference between the first relative angular position and the second relative angular position. The haptic loop is further configured to amplify the difference value by a first gain factor to produce a slave motor control signal 808, amplify the difference value by a second gain factor to produce a master motor control signal 810, and provide the slave motor control signal 808 to a slave motor control signal input of the slave gripper motor 114, and provide the master motor control signal 810 to a master motor control signal input of the master gripper motor 614. The slave motor control signal and the master motor control signal drive at least one of the slave gripper motor 114 and the master gripper motor 616 to match their respective relative angular positions with respect to the other.

Figure 11:
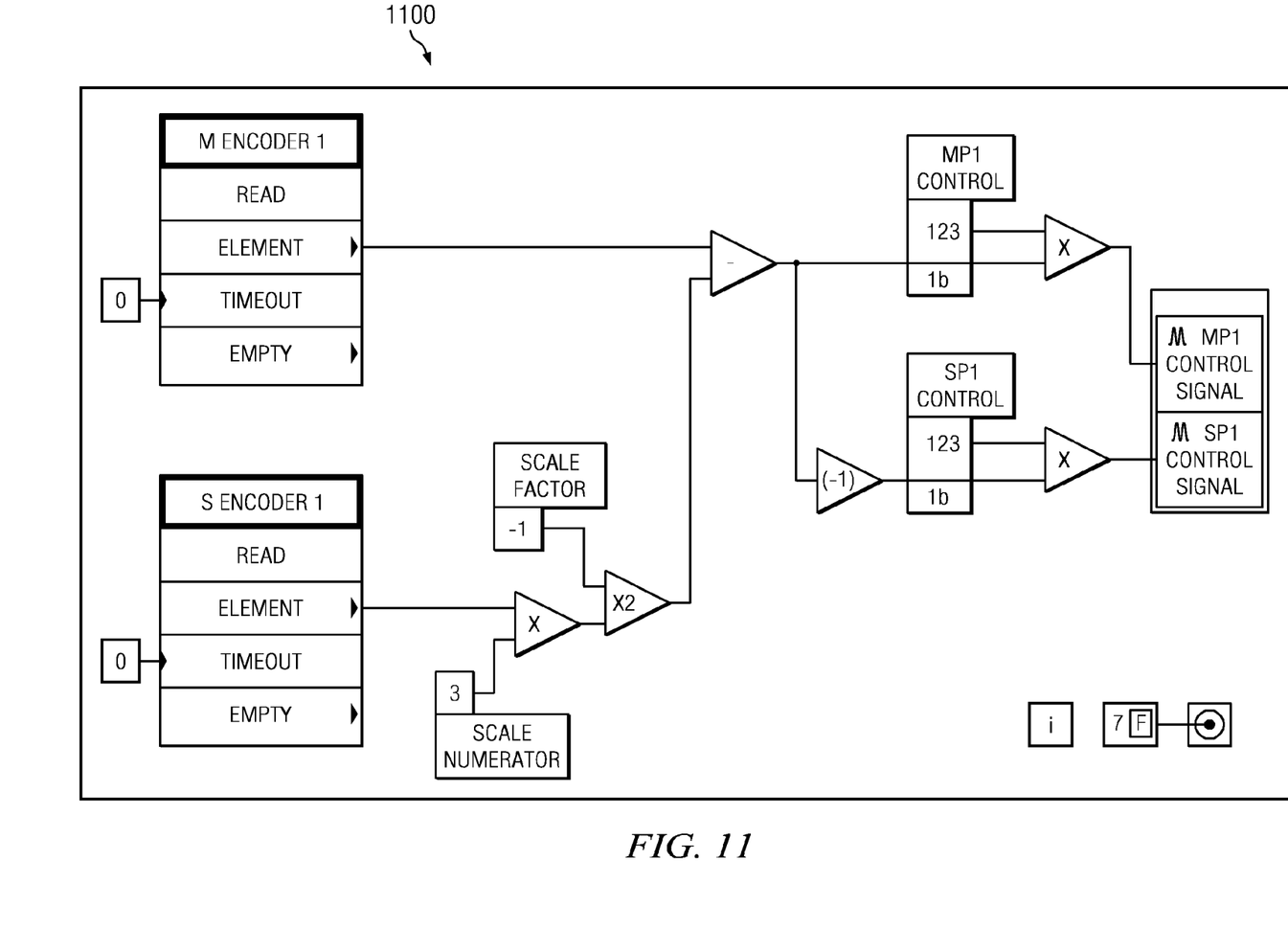
FIG. 11 illustrates an embodiment of a haptic loop.

An embodiment of a haptic loop 1100 is illustrated in FIG. 11. The haptic loop 1100 compares the counter values from the master and slave companion motor pair's encoders, and takes the difference between the slave and master encoder positions. This difference is what is desired to be corrected for so it is used to command the motors to move to the desired position. In the particular embodiment illustrated in FIG. 11, a user-controlled multiplicative gain is used to amplify the difference and output a command voltage to a motor amplifier, which will step the voltage up to driving magnitude and drive the motors to match position. In the particular illustrated embodiment of FIG. 11, there is a 1.5 scaling factor on the slave encoder and a 1.0 scaling factor on the master encoder, but it should be understood that other desired scaling factors could be used.

It will be appreciated by those skilled in the art having the benefit of this disclosure that this haptic device grippers for surgical teleoperation provides in some embodiments for bilateral position-matching between grippers of master and slave robots to provide haptic feedback to a user of the master robot. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:
1. A haptic gripper system comprising:
   a slave gripper device including:
      a slave robot body portion;
      a slave arm having a first slave arm end coupled to the slave robot body portion;

a slave elbow joint coupled to a second slave arm end of the slave arm, the slave elbow joint having a slave elbow joint hinge pin having a substantially circular cross-section and a first horizontal axis of rotation, the slave elbow joint hinge pin further having a plurality of slave elbow cable channels, wherein each slave elbow cable channel has an upper surface with a substantially parabolic cross section and a vertex positioned at a first predetermined distance below the first horizontal axis of rotation;

a slave effector having first slave effector end coupled to the slave elbow joint;

a slave gripper assembly coupled to a second slave effector end of the slave effector;

a slave gripper motor mounted to the slave arm, the slave gripper motor having a slave motor control signal input, and a first encoder configured to output a first slave motor encoder output signal and second slave motor encoder output signal;

a slave drive cable coupled between the slave gripper motor and the slave gripper assembly through at least a first slave elbow cable channel of the plurality of slave elbow cable channels and in contact with the upper surface of the at least first slave elbow cable channel, the first predetermined distance being determined such that the slave drive cable passes substantially through the first horizontal axis of rotation of the slave elbow joint hinge pin;

a master gripper device including:
  a master robot body portion;
  a master arm having a first master arm end coupled to the master robot body portion;
  a master elbow joint coupled to a second master arm end of the master arm, the master elbow joint having a master elbow joint hinge pin having a substantially circular cross-section and a second horizontal axis of rotation, the master elbow joint hinge pin further having a plurality of master elbow cable channels, wherein each master elbow cable channel has an upper surface with a substantially parabolic cross section and a vertex positioned at a second predetermined distance below the second horizontal axis of rotation;
  a master effector having first master effector end coupled to the master elbow joint;
  a master gripper assembly coupled to a second master effector end of the master effector;
  a master gripper motor mounted to the master upper link arm, the master gripper motor having a master motor control signal input, and a second encoder configured to output a first master motor encoder output signal and second master motor encoder output signal;
  a master drive cable coupled between the master gripper motor and the master gripper assembly and routed through at least a first master elbow cable channel of the plurality of master elbow cable channels and in contact with the upper surface of the at least first master elbow cable channel, the second predetermined distance being determined such that the master drive cable passes substantially through the second horizontal axis of rotation of the master elbow joint hinge pin; and a gripper motor controller including:
  a slave encoder loop having a first slave motor encoder input configured to receive the first slave motor encoder output signal, and a second slave motor encoder input configured to receive the second slave motor encoder signal, the slave encoder loop further configured to determine a first relative angular position of the slave motor based upon the first slave motor encoder output signal and the second slave motor encoder output signal and output a slave motor encoder loop output signal indicative of the first relative angular position;
  a master encoder loop having a first master motor encoder input configured to receive the first master motor encoder output signal, and a second master motor encoder input configured to receive the second master motor encoder signal, the master encoder loop further configured to determine a second relative angular position of the first master motor based upon the first master motor encoder output signal and the second master motor encoder output signal and output a master motor encoder loop output signal indicative of the second relative angular position;
  a haptic loop configured to receive the slave motor encoder loop output signal and the master motor encoder loop output signal, determine a difference signal between the slave motor encoder loop output signal and the master motor encoder loop output signal representative of a difference between the first relative angular position and the second relative angular position, amplify the difference value by a first gain factor to produce a slave motor control signal, amplify the difference value by a second gain factor to produce a master motor control signal, provide the slave motor control signal to the slave motor control signal input, and provide the master motor control signal to the master motor control signal input;
  wherein the slave motor control signal and the master motor control signal drive at least one of the slave gripper motor and the master gripper motor to match their respective relative angular positions with respect to the other.

2. A haptic gripper system comprising:
a slave gripper device including:
  a slave robot body portion;
  a slave upper link arm having a first slave upper link end coupled to the slave robot body portion;
  a slave elbow joint coupled to a second slave upper link end of the slave upper link, the slave elbow joint having a slave elbow joint hinge pin having a substantially circular cross-section and a first horizontal axis of rotation, the slave elbow joint hinge pin further having a plurality of slave elbow cable channels, wherein each slave elbow cable channel has an upper surface with a substantially parabolic cross section and a vertex positioned at a first predetermined distance below the first horizontal axis of rotation;
  a slave effector having first slave effector end coupled to the slave elbow joint;
  a slave lower link arm having a first slave lower link end coupled to the slave robot body portion and a second slave lower link end jointedly coupled to the slave effector;
  a slave gripper assembly coupled to a second slave effector end of the slave effector, the slave gripper assembly having a first slave gripper spool coupled to a first slave gripper arm and a second slave gripper spool coupled to a second slave gripper arm;
  a slave gripper motor mounted to the slave upper link arm, the slave gripper motor having a first slave motor pulley and a second slave motor pulley, the slave gripper motor further having a slave motor control signal input, and a first quadrature encoder configured to output a first slave motor encoder output signal and second slave motor encoder output signal, wherein a phase of the first slave motor encoder output signal is offset by substantially 90 degrees from a phase of the second slave motor encoder output signal;

a first slave drive cable coupled between the first slave motor pulley and the first slave gripper spool and routed through at least a first slave elbow cable channel of the plurality of slave elbow cable channels and in contact with the upper surface of the at least first slave elbow cable channel, the first predetermined distance being determined such that the first slave drive cable passes substantially through the first horizontal axis of rotation of the slave elbow joint hinge pin; and a second slave drive cable coupled between the second slave motor pulley and the second slave gripper spool and routed through at least a second slave elbow cable channel of the plurality of slave elbow cable channels and in contact with the upper surface of the at least second slave elbow cable channel, the first predetermined distance being determined such that the second slave drive cable passes substantially through the first horizontal axis of rotation of the slave elbow joint hinge pin;

a master gripper device including:
  a master robot body portion;
  a master upper link arm having a first master upper link end coupled to the master robot body portion;
  a master elbow joint coupled to a second master upper link end of the master upper link arm, the master elbow joint having a master elbow joint hinge pin having a substantially circular cross-section and a second horizontal axis of rotation, the master elbow joint hinge pin further having a plurality of master elbow cable channels, wherein each master elbow cable channel has an upper surface with a substantially parabolic cross section and a vertex positioned at a second predetermined distance below the second horizontal axis of rotation;
  a master effector having first master effector end coupled to the master elbow joint;
  a master lower link arm having a first master lower link end coupled to the slave robot body portion and a second master lower link end jointedly coupled to the slave effector;
  a master gripper assembly coupled to a second master effector end of the master effector, the master gripper assembly having a first master gripper spool coupled to a first master gripper arm and a second master gripper spool coupled to a second master gripper arm;
  a master gripper motor mounted to the master upper link arm, the master gripper motor having a first master motor pulley and a second master motor pulley, the master gripper motor further having a master motor control signal input, and a second quadrature encoder configured to output a first master motor encoder output signal and second master motor encoder output signal, wherein a phase of the first master motor encoder output signal is offset by substantially 90 degrees from a phase of the second master motor encoder output signal;
  a first master drive cable coupled between the first master motor pulley and the first master gripper spool and routed through at least a first master elbow cable channel of the plurality of master elbow cable channels and in contact with the upper surface of the at least first master elbow cable channel, the second predetermined distance being determined such that the first master drive cable passes substantially through the second horizontal axis of rotation of the master elbow joint hinge pin; and
  a second master drive cable coupled between the second master motor pulley and the second master gripper spool and routed through at least a second master elbow cable channel of the plurality of master elbow cable channels and in contact with the upper surface of the at least second master elbow cable channel, the first predetermined distance being determined such that the second master drive cable passes substantially through the second horizontal axis of rotation of the master elbow joint hinge pin; and a gripper motor controller including:
  a slave encoder loop having a first slave motor encoder input configured to receive the first slave motor encoder output signal, and a second slave motor encoder input configured to receive the second slave motor encoder signal, the slave encoder loop further configured to determine a first relative angular position of the slave motor based upon the first slave motor encoder output signal and the second slave motor encoder output signal and output a slave motor encoder loop output signal indicative of the first relative angular position;
  a master encoder loop having a first master motor encoder input configured to receive the first master motor encoder output signal, and a second master motor encoder input configured to receive the second master motor encoder signal, the master encoder loop further configured to determine a second relative angular position of the first master motor based upon the first master motor encoder output signal and the second master motor encoder output signal and output a master motor encoder loop output signal indicative of the second relative angular position;
  a haptic loop configured to receive the slave motor encoder loop output signal and the master motor encoder loop output signal, determine a difference signal between the slave motor encoder loop output signal and the master motor encoder loop output signal representative of a difference between the first relative angular position and the second relative angular position, amplify the difference value by a first gain factor to produce a slave motor control signal, amplify the difference value by a second gain factor to produce a master motor control signal, provide the slave motor control signal to the slave motor control signal input, and provide the master motor control signal to the master motor control signal input;
  wherein the slave motor control signal and the master motor control signal drive at least one of the slave gripper motor and the master gripper motor to match their respective relative angular positions with respect to the other.

* * * * *